United States Patent [19]
Rosen

[11] Patent Number: 5,345,810
[45] Date of Patent: Sep. 13, 1994

[54] NORMALIZED RELATIVE HUMIDITY PROCESS

[76] Inventor: Jay Rosen, 142 Friedley Ave., Bellevue, Ohio 44811

[21] Appl. No.: 163,504

[22] Filed: Dec. 9, 1993

Related U.S. Application Data

[62] Division of Ser. No. 895,089, Jun. 8, 1992.

[51] Int. Cl.$^5$ .............................................. G01W 1/00
[52] U.S. Cl. .................................................. 73/29.02
[58] Field of Search ................ 73/29.02, 29.01, 335.02

[56] References Cited

U.S. PATENT DOCUMENTS 5,005,410  4/1991  Webster et al. .................. 73/335.02

*Primary Examiner*—Hezron E. Williams
*Assistant Examiner*—Joseph W. Roskos

[57] ABSTRACT

A humidity measurement process and humidity measurement scale are derived from the physics of relative humidity. Absolute moisture content is determined independent of any measurement or knowledge of the source temperature. The humidity measurement is equivalent to the volumetric fraction of water vapor in the measured gas mixture, expressed as a percentage in a fixed range from 0 to 100%. The operating principles of the measurement process and measurement scale are described for use with an instrument suitable for humidity measurements in process ovens, product dryers, exhaust stacks, and similar environments operating at temperatures to 1250° F. and near atmospheric pressure. The instrument is a point-source sampling system. A continuous sample of process air is induced to flow through the instrument for humidity measurement. The temperature of the sample is regulated to a constant measurement temperature above the dew point temperature of the source, and below the operational temperature limit of a solid state relative humidity sensor. Moisture content is calculated from the sensed relative humidity at constant temperature and the absolute measurement pressure. Temperature is not a parameter in the humidity calculation.

4 Claims, 10 Drawing Sheets

NORMALIZED RELATIVE HUMIDITY PROCESS

This is a divisional application of Ser. No. 07/895,089; filed Jun. 8, 1992.

BACKGROUND OF THE INVENTION

1. Field of the Invention

The present invention relates to humidity measurement. The invention describes an instrument, process, and measurement scale for determining absolute moisture content, independent of any measurement of the humidity source temperature. The operating principles are suitable for use in industrial high temperature applications.

2. Description of the Prior Art

The art of psychrometry and specifically humidity measurement continues to be a difficult subject area for both laymen and technical personnel. Misunderstanding of the subject matter is compounded by the use of multiple measurement scales. Relative moisture scales, such as relative humidity and wet bulb temperature, require a secondary measurement of the ambient source temperature. Absolute moisture scales, such as dew point temperature and humidity ratio, are independent of source temperature. Conversion between scales requires extensive psychrometric tables and graphs. Data at elevated temperatures, high humidity levels, and altitudes other than sea level is not widely circulated.

The choice of measurement scale and use of absolute or relative measurements, reflects the application and user expertise. Relative humidity is usually of greatest interest in material processes, as low relative humidity may cause brittleness or problems with static electricity. High relative humidity values may cause an undesirable surface texture, swelling, or clumping regardless of temperature. Meteorologists report relative humidity and the ambient dry bulb temperature in weather data to reflect an environmental comfort level. Historically, wet bulb temperatures have also been measured and reported as a humidity indicator for weather and energy management use. Dew point temperature may be used in a process where dryness of the atmosphere is desirable to avoid condensation at low temperatures. Humidity ratios are typical in drying and other mass transfer processes, where water vapor is an important component in the manufacturing process.

The instrumentation required for humidity measurement has also been largely influenced by the measurement scale of preference. Instruments may be simple and mechanical or sophisticated and electronic. Fully mechanical hygrometers based on material dimensional changes with relative humidity are common. Wet bulb temperature is derived from sling psychrometers or air movement across similar temperature devices clothed in capillary wicking. Optical, chilled mirror systems are available for dew point measurements. Solid state sensors which change capacitance or resistance with relative humidity are increasingly prevalent.

HVAC, meteorological, energy measurement, and light manufacturing industries require humidity measurements and control at ordinary temperatures. Much of the commercially available humidity measuring equipment, measurement scales, and psychrometric literature are directed to these users. There are many commercial and industrial applications which require humidity measurement and control at elevated temperatures. Drying industries, particularly, those in paper, textiles, and building materials, food processors and chemical product manufacturers are representative. These industries operate processes well above 212° F., to 600° F. and higher, and at pressures above and below atmospheric sea level. Consistent and understandable humidity physics and measurements suitable for process control at elevated temperature are required.

To date, no single instrument or humidity measure has proven satisfactory for all applications.

SUMMARY OF THE INVENTION

The primary object of the invention is to establish a method of humidity measurement suitable for broad application in science and industry. The method is compatible for use with existing, proven, and cost-effective relative humidity sensor technology. Solid state measurement devices, such as thin film capacitance and resistive relative humidity sensors are recommended. Humidity measurements are defined strictly by absolute moisture content. Measurement or previous knowledge of the humidity source temperature is not required. The measurement process is suitable for determining humidity at the elevated temperatures commonly encountered in industrial processing.

A second objective is to develop a fundamental humidity measurement scale. The measurement scale integrates the advantages of an absolute moisture scale with the simplicity and understanding of a relative moisture scale. The quantitative values are physically descriptive of the humidity measurement. The measurement scale is a mathematical construction from 0 to 100%. The percentage is equivalent to the volumetric fraction of water vapor in the measured gas mixture. The humidity measurement scale is designated normalized relative humidity. Values of normalized relative humidity, for ease of conversation, may be further designated RHN or % RHN. The term reflects a definitive relationship with relative humidity principles, but without the requirement of a known dry bulb temperature.

A third objective is to provide the means to reference normalized relative humidity measurements to other humidity scales. Equations suitable for calculation by electrical circuits are shown. The mathematics for correcting the humidity measurement for local barometric altitude is also provided.

Implicit in the use of the RHN scale is the intuitive understanding that develops from measuring humidity in the context of fractional volumes. Industrial processes are defined by concepts that are inherently volume based. Enclosure dimensions, fan flow rates exhaust stack flow emissions, make-up air requirements, and many other engineering calculations are reported in volume terms. The simple multiplication of mixture volume by RHN can be used to calculate the water vapor volume. At a known process temperature, RHN may be simply used in mass and energy balance calculations, particularly important in the drying industries.

Absolute moisture content is calculated by measuring relative humidity at a precisely maintained constant temperature. Humidity calculations involving temperature are not required. The constant temperature value is above the boiling point of water and below sensor material limits. The process is calibrated by correlating values of measured relative humidity at constant temperature with relative humidity at full saturation at all temperatures up to and including the boiling point. The relative humidity measurement at constant temperature is scaled to a range of 0 to 100%. The percentage is a ratio of the partial pressure of water vapor in the measured atmosphere, to the total gas mixture pressure. Ideal gas laws are used to show the equivalence of this partial pressure ratio to the volumetric fraction of water vapor in the gas mixture.

DESCRIPTION OF THE DRAWINGS

A more complete appreciation of the invention will be clearly apparent from a consideration of the following drawings and description wherein.

DESCRIPTION OF THE PREFERRED EMBODIMENT

1. Ideal Gas Properties

Water vapor is a gas. Water vapor may exist solely at a defined saturation pressure and temperature, or as a component in a mixture of other compatible gases. Though any mixture of non-reacting gases may be similarly treated, the following discussion is to be understood in terms of process air. Process air is primarily a homogeneous mixture of dry air and water vapor. Common process air environments include conveyorized ovens and dryers, exhaust stacks, and vented batch processes. The ambient pressure in these environments is nearly equivalent to the prevailing external atmospheric pressure. Water vapor may be found from zero to full saturation within these enclosures and at virtually any temperature.

Figure 1:
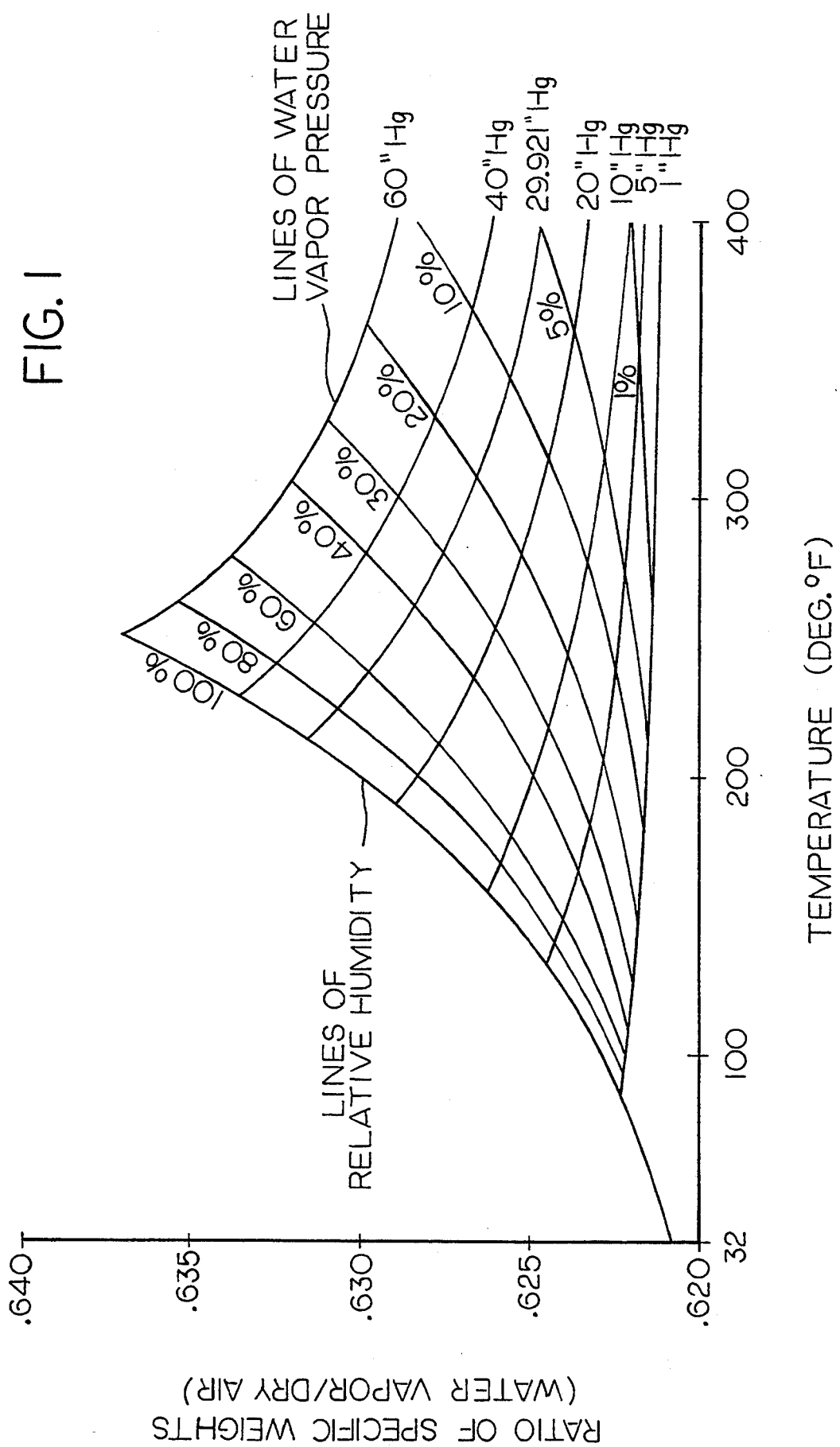
FIG. 1 is a graph of the specific weight of water vapor to dry air; where water vapor is shown to be an ideal gas over a wide range of temperatures and levels of saturation.

In FIG. 1, the ratio of the specific weight of water vapor to dry air at the same temperature and varying levels of saturation is graphically shown. Little change in specific weight is noted over what may be considered common processing pressures (full vacuum to two atmospheres) and a wide range in temperature. Relative to dry air, an average specific weight ratio of 0.622 is utilized. At higher temperatures and all pressures near atmospheric, water vapor approximates an ideal gas.

2. Amagat Model of Volumetric Fractions

In the thermodynamic Amagat model, the properties of ideal gases are considered as though each gas component existed separately at the pressure and temperature of the gas mixture. The Amagat model states that the sum of the volumes of the respective gases are equivalent to the total volume, if the components are mixed at constant temperature and pressure.

For the mixture total volume, Vt, we can write:

$$Vt = Vw + Va \qquad (1)$$

where Vw, and Va are the fractional volumes of water vapor and air respectively.

Similarly, for water vapor as a component in a mixture of ideal gases, the volumetric fraction, mol fraction, and partial pressure ratio of water vapor to the total mixture volume, mols, and pressure are equivalent:

$$\frac{Vw}{Vt} = \frac{Yw}{Yt} = \frac{Pw}{Pt} \qquad (2)$$

where V, Y and P represent volume, mols, and pressure respectively. Subscripts w and t are water vapor and total mixture properties respectively.

The volumetric fraction is the ratio of the gas partial volume to the overall mixture volume. The partial volume is the volume the gas would occupy at the mixture temperature and pressure.

3. Relative Humidity

Relative humidity, commonly referred to as RH, is familiar from the meteorological use as an everyday indicator of atmospheric humidity. RH is the moisture content of air relative to saturation at the measured dry bulb temperature. Being a ratio, RH is invariably expressed as a percentage. A 100% RH atmosphere is a fully saturated, condensing atmosphere. A 0% RH atmosphere is dry air. Dry air, by convention, contains no water vapor.

Relative humidity is strictly defined as the partial pressure of water vapor, Pw, in the atmosphere to that of the saturation water vapor pressure, Ps, at the identical dry bulb temperature.

$$\% RH = \frac{Pw}{Ps} \times 100 \qquad (3)$$

This technical definition and our everyday experience with RH are in agreement up to the temperature at which water boils; i.e., 212° F., at 1 ATM.

In a high temperature process open to atmosphere—a conveyorized oven, exhaust stack, etc.—the pressure in these enclosures is essentially that of the prevailing external atmospheric pressure. The pressure is also equivalent to the sum of the partial pressures of the individual gases in the atmospheric mixture. It follows that the sum of the partial pressure of water vapor, Pw, and partial pressure of dry air, Pa, must be equivalent to the external atmospheric pressure, Patm; such that Patm=Pw+Pa.

At temperatures above the boiling point, water vapor could displace all other gases in the enclosure. The atmosphere would then consist entirely of superheated steam. In this atmosphere, the partial pressure of water vapor, Pw, in the process is equivalent to the external atmospheric pressure, Patm; such that Patm=Pw. The maximum values of relative humidity at temperatures above the boiling point may be calculated.

$$\text{Maximum \% } RH = \frac{Patm}{Ps} \times 100 \qquad (4)$$

Figure 2:
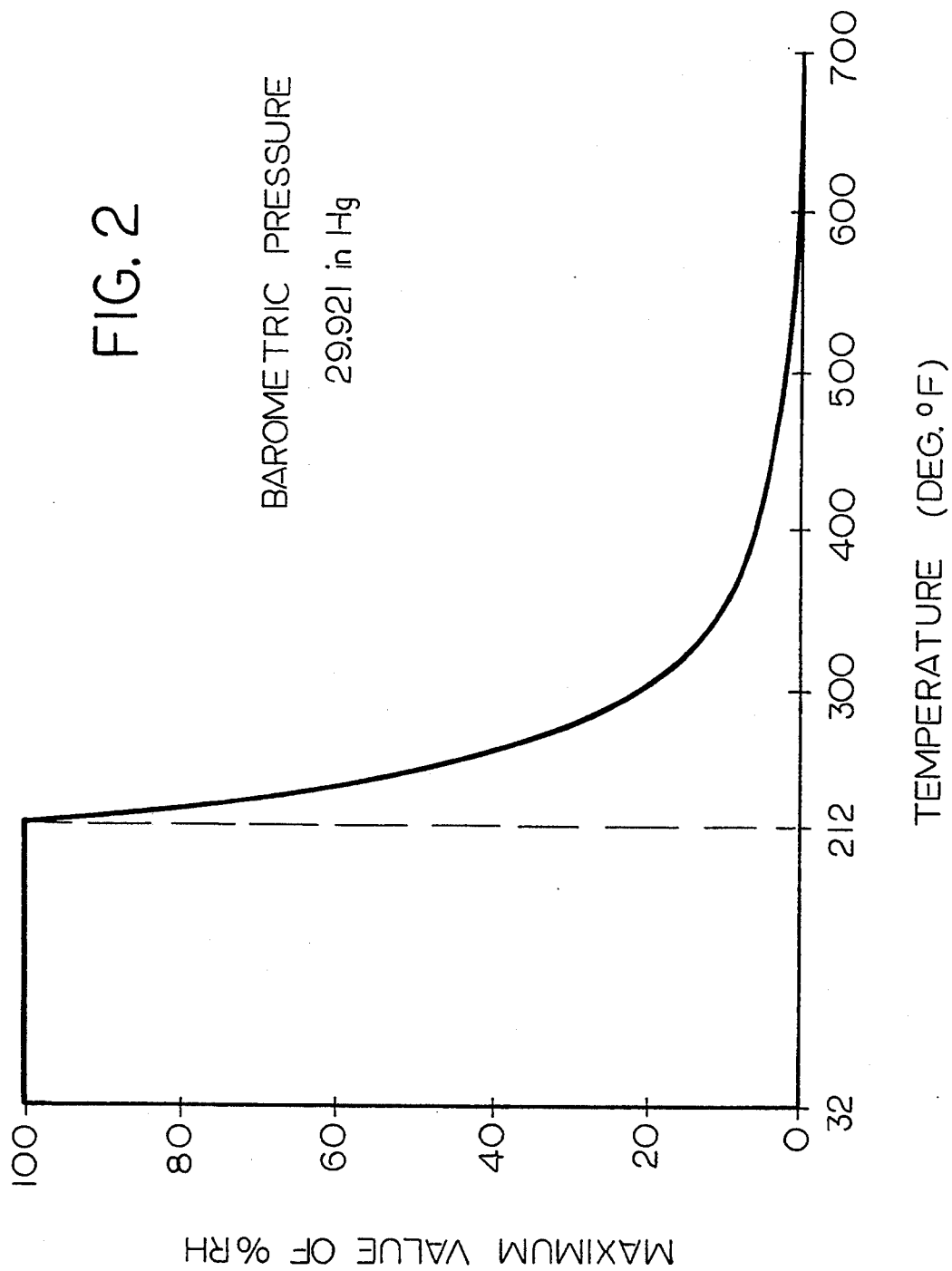
FIG. 2 is a graph of the maximum percentage values of relative humidity at atmospheric pressure; where maximum percentage relative humidity declines in value with increasing temperature above the boiling point.

Since the saturation pressure, Ps, is always greater than that of atmospheric above 212° F., the maximum value of % RH at temperatures above the boiling point is always less than 100%! Above 212° F., the use of relative humidity is a misleading indicator of moisture content. A process atmosphere of fixed and constant humidity content, would have a declining value of relative humidity with increasing temperature, FIG. 2. At sea level atmospheric pressure and dry bulb temperature of 212° F., the maximum value of % RH is 100%. At 400° F., the maximum value of % RH is approximately 5.9%. At 700° F., the maximum value of % RH is approximately 0.5%. Relative humidity is undefined at temperatures above 705.4° F., the critical point of water. Saturation pressures above this temperature are not thermodynamically specified.

4. Normalized Relative Humidity

Normalized relative humidity, utilizes the physics and measurement principles of relative humidity in a useful and novel form, without the above limitations. Normalized relative humidity is a percentage measurement scale of quantitative values in a fixed range of 0 to 100%. Normalized relative humidity values, designated RHN or % RHN, are equivalent to the volumetric fraction of water vapor in the measured gas mixture, multiplied by 100 to obtain a percentage. Similarly, RHN percentage values are equivalent to the partial pressure ratio of water vapor to the absolute pressure of the measured gas mixture. RHN percentage values are also equivalent to the mol fraction of water vapor in the measured gas mixture. The RHN measurement scale is a direct measure of absolute moisture content. RHN percentage values are determined independently and without previous knowledge of the humidity source temperature.

The RHN percentage is calculated by dividing equation (3) by (4); where equation (3) represents relative humidity measured at a dry bulb temperature, and equation (4) represents a ratio of the absolute measurement pressure to the saturation water vapor pressure defined at that dry bulb temperature. The result is a ratio of two pressures:

$$\text{\% } RHN = \frac{Pw}{Patm} \times 100 \qquad (5)$$

where Pw is the partial pressure of water vapor, and Patm is generally tile ambient atmospheric pressure, and specifically the absolute measurement pressure. The partial pressure of water vapor and the absolute measurement pressure are constant physical parameters of the measured gas mixture. Dry bulb temperature is not required in the humidity calculation. The saturation water vapor pressure which is a temperature dependent parameter, is mathematically eliminated in the calculation.

The RHN humidity scale is physically descriptive of the humidity measurement. The Amagat model of gas mixtures states the equivalence of the partial pressure ratio to volumetric fraction. The ratio of partial pressure to total process pressure is equivalent to the volumetric fraction of water vapor to the total volume. A 100% RHN process atmosphere is that of pure water vapor. A 50% RHN atmosphere is 50% water vapor by volume. A 0% RHN process atmosphere can include any constituent except water vapor.

RHN is linear with changes in relative humidity at temperatures above the boiling point of water. Values of RHN represent the percentage of the maximum value of relative humidity at any temperature above saturation temperature where saturation pressures are thermodynamically specified. As an example, consider an atmosphere at 400° F., 1 Atm. The maximum % RH was shown to be 5.9%. A 100% RHN atmosphere at this temperature is a 5.9% RH atmosphere. A RHN value of 50% generated at this temperature is equivalent to 50% of 5.9%, or roughly 2.9% RH. A RHN value of 10% at this temperature is equivalent to 10% of 5.9%, or roughly 0.6% RH. Note that RHN is normalized with respect to the maximum value of % RH.

Figure 3A:
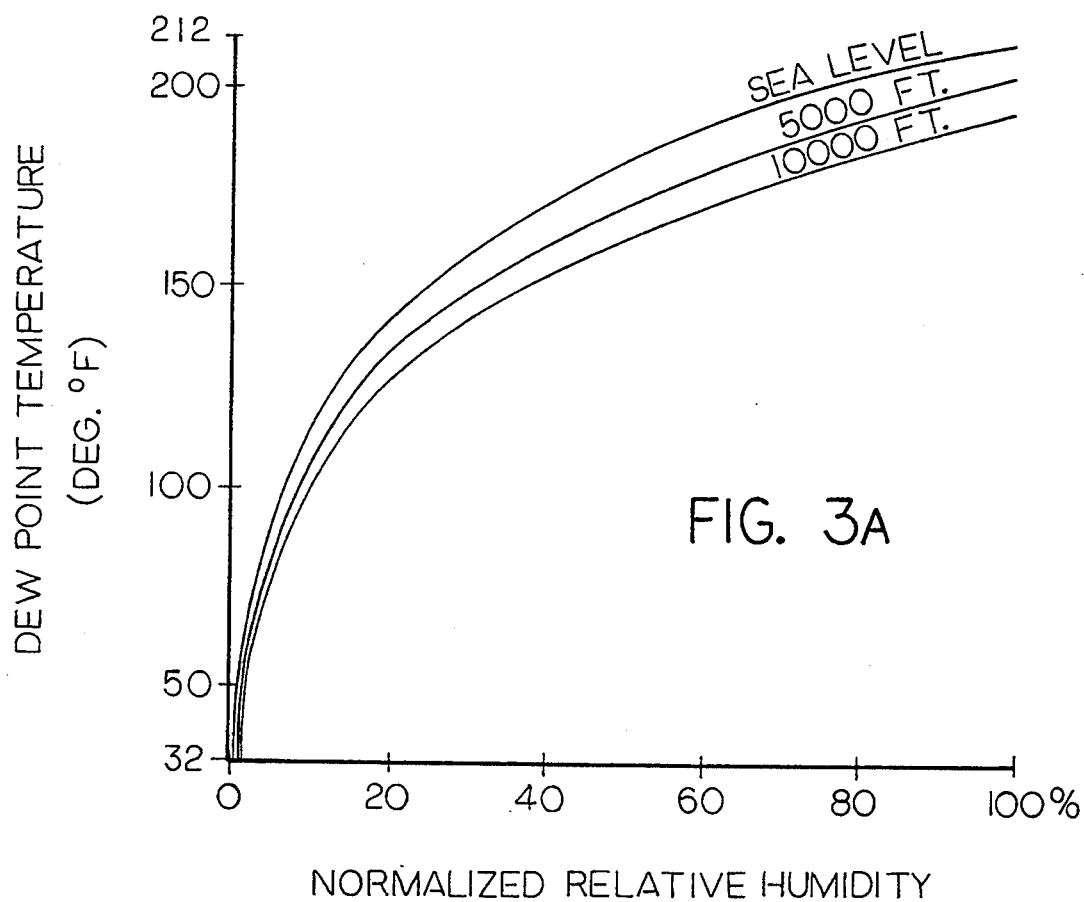
FIG. 3A is a graph of dew point temperatures at varying elevations corresponding to values of normalized relative humidity.
Figure 3B:
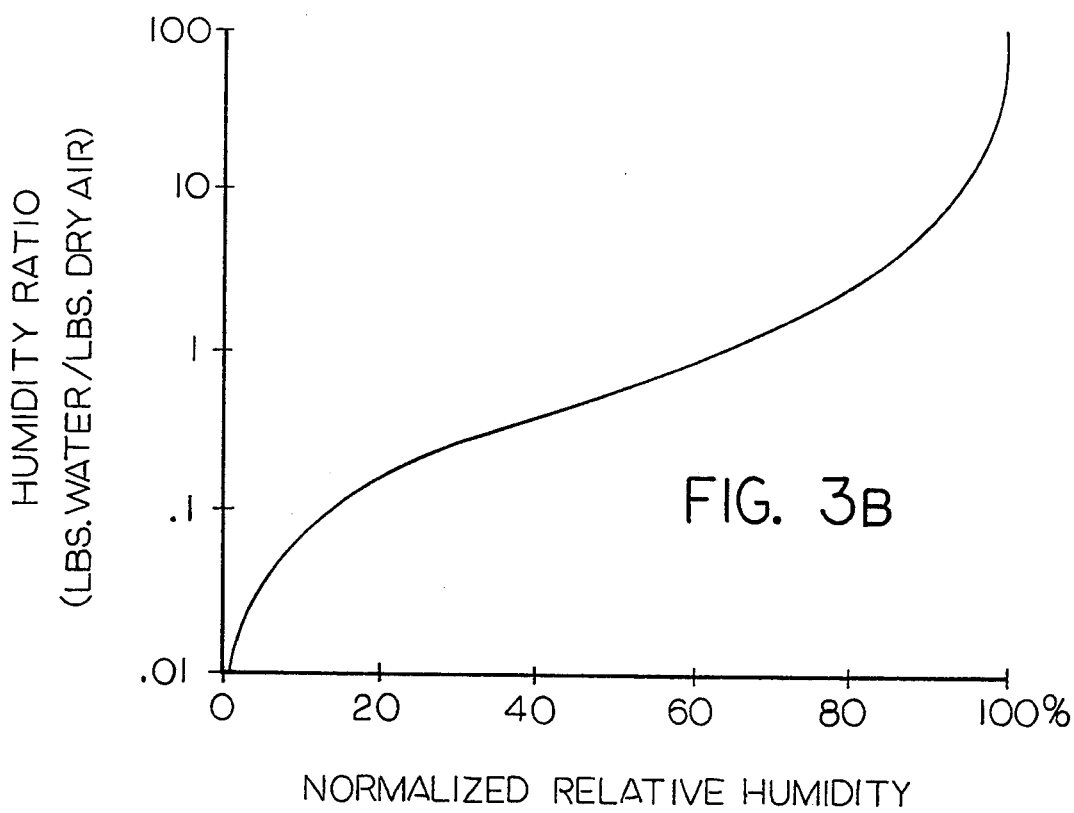
FIG. 3B is a graph of the humidity ratio corresponding to values of normalized relative humidity.

Normalized relative humidity may be correlated with any known measure of humidity, including dew point temperature and humidity ratio. FIG. 3A and FIG. 3B graphically represent these relationships. Dew Point temperature is the temperature at which water vapor will condense when cooled at constant pressure. RHN may be correlated with dew point temperature by an accurate calculation of the saturation water vapor pressure over liquid water, in the range 32° F. to 212° F. at 1 ATM. The saturation water vapor pressure is calculated at the dew point temperature by the Keenan-Keyes formula, published in the ASHRAE Handbook of Fundamentals, 1985:

$$Pw = 6527.8 \times 10^{(A \times B)} \qquad (6)$$

where:
Pw=saturation water vapor pressure, inches Hg
$A = -\beta/T$
$B = (a + b\beta + c\beta^3)/(1 + d\beta)$
$\beta = 647.27 - T$
T=absolute temperature, degrees Kelvin
$a = 3.2437814$
$b = 5.86826 \times 10^{-3}$
$c = 1.1702379 \times 10^{-8}$
$d = 2.1878462 \times 10^{-3}$ The saturation water vapor pressure is then divided by the ambient total pressure at which RHN is measured and multiplied by 100 to calculate RHN. Humidity or mixing ratio is the mass ratio of water vapor to dry air. RHN may be correlated by the following equation.

$$W = \frac{RHN \times S}{100 - RHN} \qquad (7)$$

where:
W is the humidity or mixing ratio (lbs. of water/lbs. of air),

S is the ratio of the specific weight of water vapor to air at the same temperature and pressure, as shown in FIG. 1, or 0.622 for most practical applications.

5. RHN and Barometric Pressure

The absolute measurement pressure is required in the calculation of normalized relative humidity. In the majority of process applications, the measurement pressure is equal to atmospheric barometric pressure. A process enclosure or vessel with openings to the external environment, such as a conveyorized oven or exhaust stack, have internal pressures which remain in balance with that of the external atmospheric pressure. Pressure variations due to fan static pressures and weather phenomena are a small fraction of the absolute atmospheric pressure and may be neglected for practical measurement purposes.

Figure 4A:
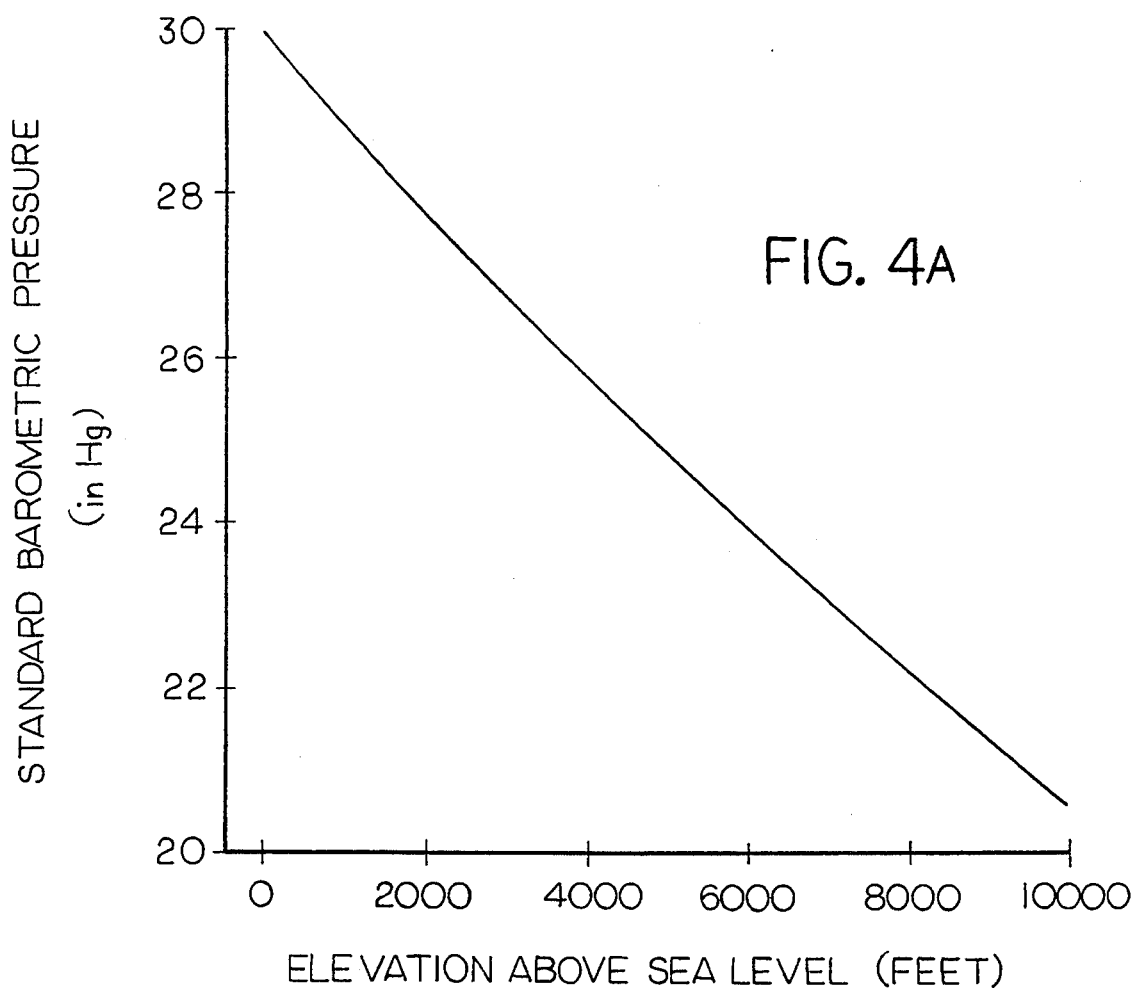
FIG. 4A is a graph of the standard barometric pressure at elevations to 10,000 feet; where standard barometric pressure is approximately linear with elevation.
Figure 4B:
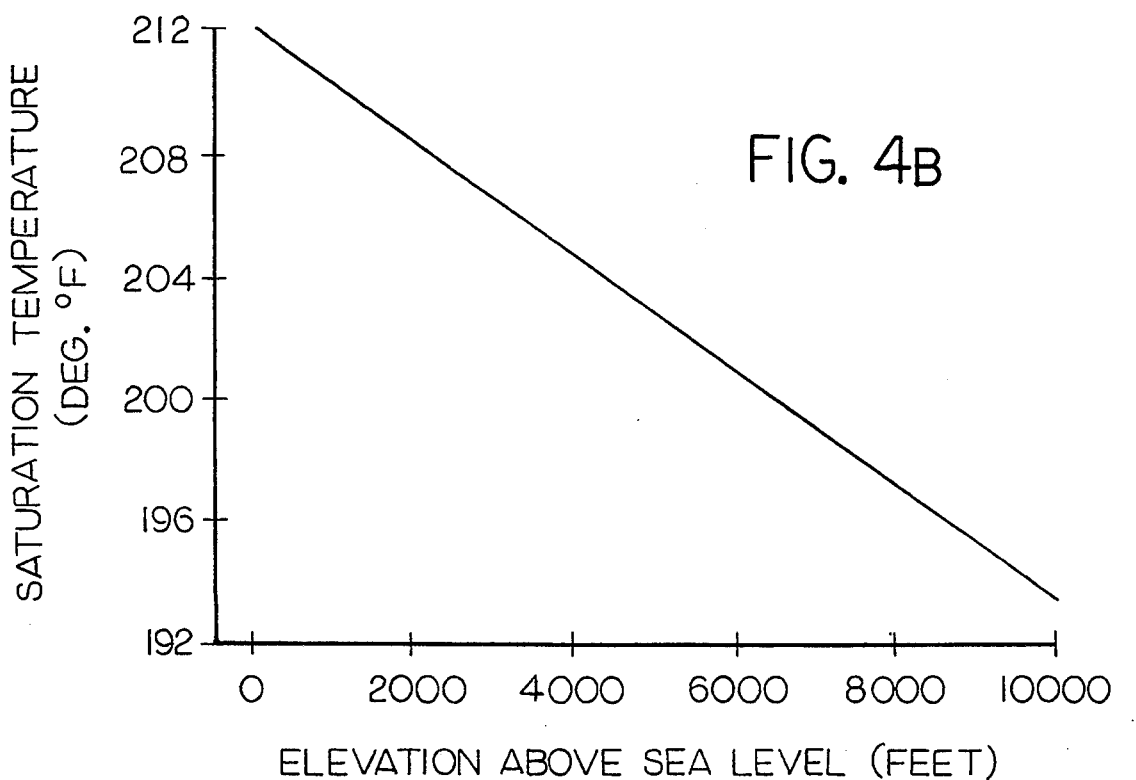
FIG. 4B is a graph of the saturation temperature or boiling point of water at standard barometric pressure for elevations to 10,000 feet.

Absolute measurement pressure, may be determined by correlation with standard barometric pressure at the elevation above sea level at which normalized relative humidity is measured. The standard barometric pressure over a wide range of altitudes is specified in the ASHRAE Brochure on Psychrometry, 1977.

$$Pb = 29.921(1 - 6.87535 \times 10^{-6} \times Z)^{5.2561} \quad (8)$$

where:

$Pb$ = standard barometric pressure, inches Hg
$Z$ = Altitude in feet above sea level This equation is approximately linear from sea level to altitudes of 10,000 ft., FIG. 4A. The saturation temperature at atmospheric barometric pressure for each elevation increment is also noted, FIG. 4B. Absolute moisture content measured in values of normalized relative humidity is essentially constant over a range of measurement pressures from near vacuum to two atmospheres. Process elevations can be assumed to be between sea level and 6,000 feet. Values of RHN at any process elevation are equal to the RHN value at a second process elevation. As a component in a mixture of ideal gases, the volumetric fraction of water vapor to mixture volume changes correspondingly with the partial pressure of water vapor to mixture pressure.

Figure 5:
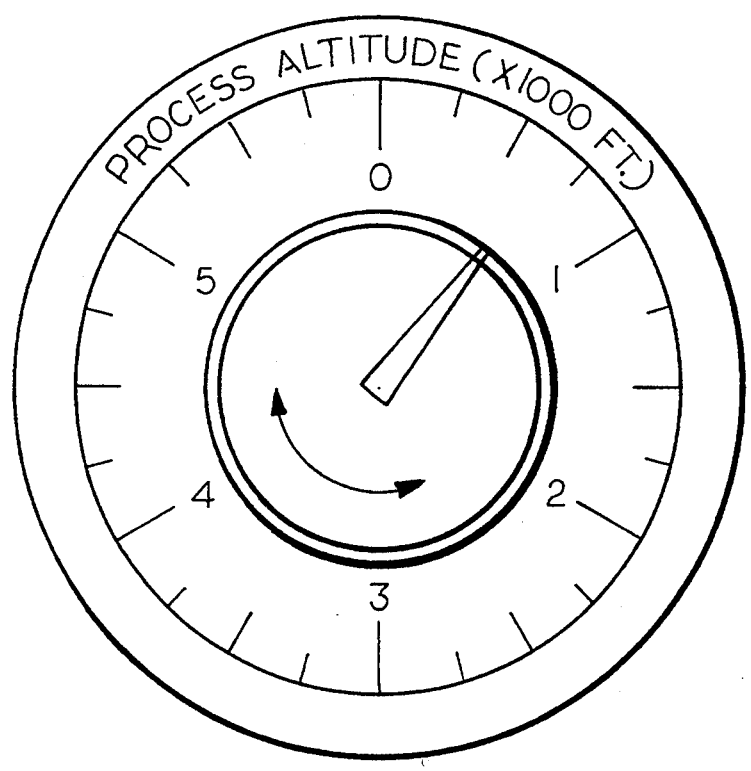
FIG. 5 represents a calibrated device such that the absolute measurement pressure can be determined from the measurement elevation above sea level; where the device is integrated within an instrument for electronic calculations of normalized relative humidity.

An instrument calculating normalized relative humidity must be adjusted for absolute measurement pressure. RHN calculations from process atmospheres where the ambient source pressure is nearly that of the external barometric pressure, can incorporate the linear relationship of equation (8) within the electronics of the measurement device. For example, FIG. 5 represents a high precision, rotary potentiometer and calibrated background altitude scale. The scale markings reflect elevation in one thousand foot increments. A keyed shaft extends through the altitude scale. A cap with an indicator pointer mates to the shaft and overlays the scale. The pointer on the cap is set to the elevation at which RHN is measured. Rotating the potentiometer shaft changes the resistance within a simple electrical circuit. Measured RHN values are then electronically compensated to output a RHN value referenced to the indicated altitude. Alternatively, an absolute measurement pressure determined by barometer instrumentation, may be integrated at the point of RHN measurement to calculate precise humidity results.

6. RHN Measurement Process

Normalized relative humidity is measured with a solid state, relative humidity sensor. The sensor is calibrated in a varying humidity atmosphere, precisely maintained at a constant temperature. Subsequent humidity measurements are determined by exposure of the calibrated RH sensor to water vapor atmospheres at the same constant measurement temperature. Humidity calculations involving temperature are not required. Values of relative humidity, measured at a constant temperature, are a direct measure of absolute moisture content.

Constant measurement temperatures are maintained above the dew point temperature of the humidity source. To prevent any probability of condensation, the constant measurement temperature should exceed the saturation temperature at the measurement pressure. Measurement temperatures are selected below the operational temperature limit of a humidity measurement sensor. A continuous sample of the humidity source is regulated by suitable heat transfer means to a constant measurement temperature and induced to flow over the RH sensor. The RH sensor measures relative humidity at the constant measurement temperature. The relative humidity value is electronically divided by a scaling factor. The scaling factor is equivalent to the absolute measurement pressure at the location of the sensor, divided by the saturation water vapor pressure, which is known at the constant temperature. The result is a ratio of the partial pressure of water to the absolute pressure of the measured gas mixture at the sensor location. The ratio is multiplied by 100 to obtain a percentage from 0 to 100%. The percentage is shown by the thermodynamics of Amagat's Law to be equivalent to the volumetric fraction of water vapor in the total gas mixture. The percentage is derived independent of any measurement or knowledge of temperature at the humidity source. The percentage values of normalized relative humidity are a measure of absolute moisture constant. Other humidity scales, independent of dry bulb temperature such as humidity ratio and dew point temperature may be calculated from RHN values.

7. Summary of Instrument

An industrial humidity measuring instrument is described. The instrument reduces to practice the fundamental principles of normalized relative humidity. The instrument is suitable for use with processing ovens, product dryers, and exhaust stacks operating at high temperatures and near atmospheric pressure. Moisture content is derived independent of any temperature measurement at the humidity source. Humidity may be measured in ambient temperatures to 1250° F. The device is equally suitable for measurements at lower ambient temperatures to a practical limit of 70° F. The instrument is designed as a point source, sampling system. Moisture content of the measured process atmosphere is determined and converted to a usable electrical output signal. A continuous sample of the humidity source atmosphere is regulated to a controlled measurement temperature. This temperature is maintained above the boiling point of water at the prevailing barometric pressure. The measurement temperature is selected to prevent any possibility of condensation, irrespective of the atmospheric dew point temperature at the source. Proven humidity and temperature sensor technology is utilized in a novel form. The temperature at the sensor location is well below the operational limits of thin film polymer RH sensors or equivalent solid state, hydroscopic devices. The instrument is calibrated at the setpoint, constant temperature, over the range of 0 to 100% RHN. Humidity calculations involving temperature are not required. The relative humidity measured at constant temperature is an exact measure of absolute moisture content.

8. Physical Description of Instrument

Figure 6:
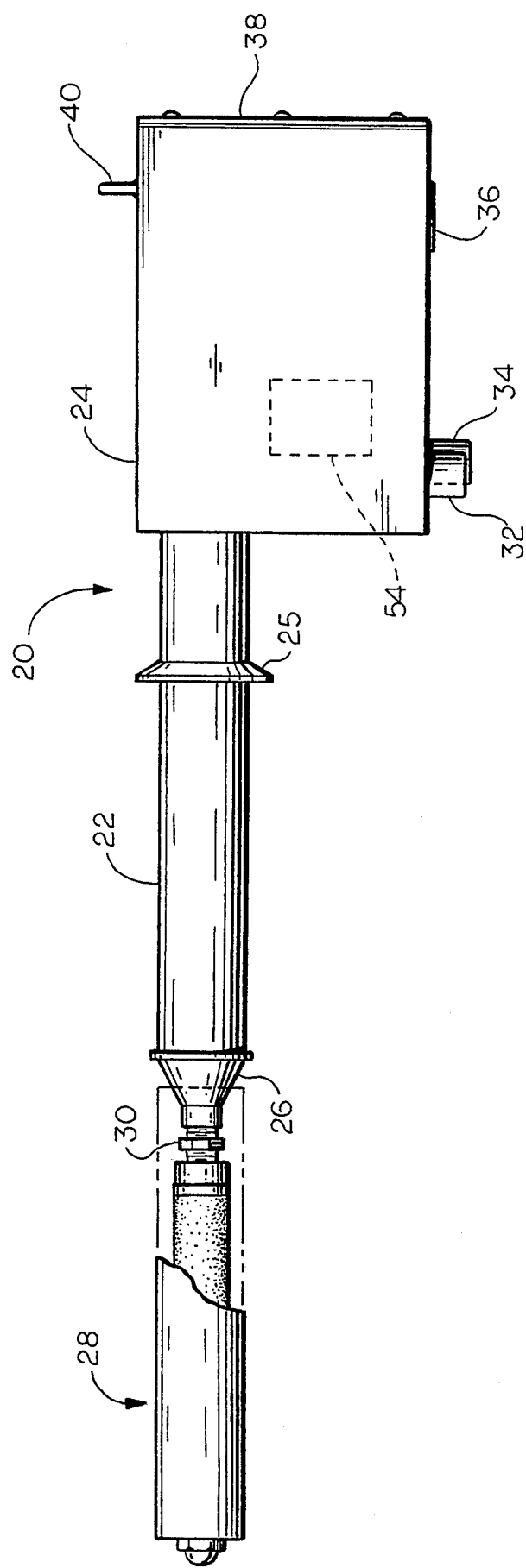
FIG. 6 is a sketch of an industrial instrument probe suitable for high temperature applications where humidity is determined in values of normalized relative humidity.

Referring to FIG. 6, the instrument probe 20 is constructed as a point source, sampling system. A continuum of humidity measurements are performed in an automated fashion without an interactive operator, at potentially high process temperatures, and contaminated atmospheres. The probe 20 is externally protected within a dust and water-tight housing, suitable for portable or permanent installation, and applications where corrosive chemical washdown conditions may exist. The present invention is fabricated as a continuously welded housing constructed entirely of materials resistant to high temperature and corrosive environments, such as 300 series stainless steel. A probe barrel 22 and rectangular probe back 24 distinguish the probe 20 shape. The external features of the probe 20 are further characterized by a tapered port 26. The port 26 is threaded to support the filter assembly 28 by pipe connector 30. Two threaded couplings for use as a compressed air inlet 32 and condensate drain 34 are welded over through holes in the probe 20 bottom. Wiring to the probe 20 is connected to any water-tight electrical connector extending through a knockout hole 36. Integral electronic and pneumatic components are located in the probe back 24. Access to the components is provided through a detachable, gasketed cover plate 38 secured to the probe back 24, by screws around the cover plate 38 perimeter. A U-Bolt 40 is suitably attached to the top surface of probe back 24. The U-Bolt 40 is connected to a snap-hook and safety chain (not shown), to hang the probe during filter maintenance or general inspection.

Figure 7:
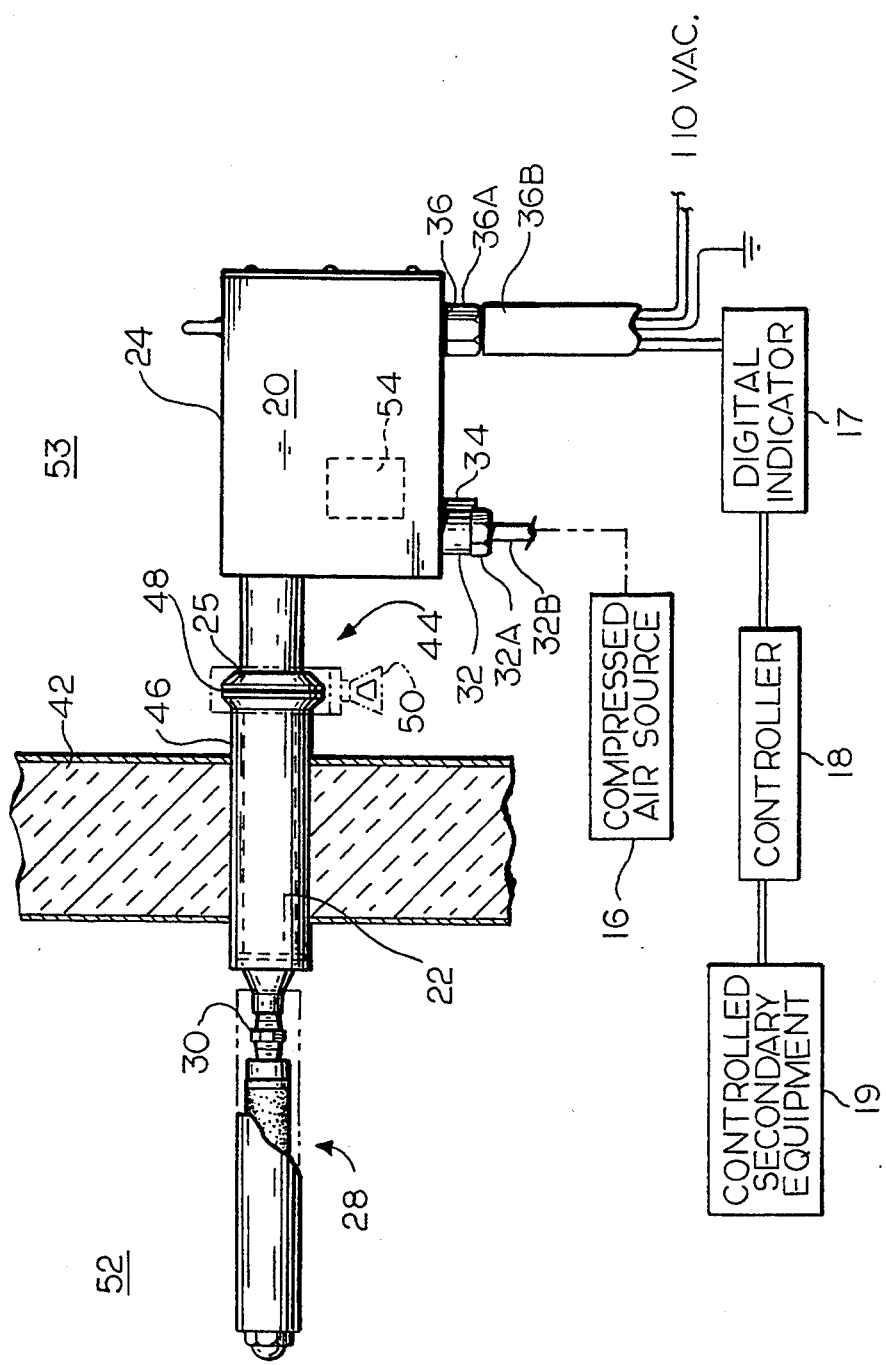
FIG. 7 is an installation schematic of the instrument probe inserted through the wall of a process oven or equivalent with the utility connections in place.

Referring to FIG. 7, the probe barrel 22 is inserted through an enclosure wall 42, and connected within a mounting tube 46 of specialized construction. The probe is externally cantilevered from the enclosure wall 42 while fully supported by the clamp assembly 44. Welded to the probe barrel 22, is a sealing cap 25 which mates to a similarly shaped flange of mounting tube 46. A gasket 48, preferably teflon, is held in compression between the sealing cap 25 and the mounting tube 46 by a removable wing nut clamp 50. The clamp 50, gasket 48, cap 25, and flange on mounting tube 46 are manufactured to connect process tubing in a gas and liquid-tight manner. The manufacturer is Tri-Clover, Inc. of Kenosha, Wis.

The process atmosphere is induced to flow through the probe 20 by means of a slight negative pressure generated preferably by an aspirating venturi pump 54. The venturi pump 54 housed in probe back 24, requires compressed air as the motive fluid. In the preferred embodiment, the compressed air source 16 is an electrically driven diaphragm pump. Compressed air requirements of 0.5 CFM at 5 to 10 psi are adequate. Compressed air is supplied to the venturi pump 54 by flexible tubing 32B connected to a compression or barbed fitting 32A threaded into the compressed air inlet 32.

Power and signal wires in conduit 36B interfaces the probe 20 to auxiliary equipment and line power. The conduit 36B is mated to a electrical connector 36A connected through a knockout hole 36 in the probe 20 housing. Electrical requirements are common line power voltage 110 V with ground, 3 Amps maximum.

An in-line filter assembly 28 prevents air-borne product contaminants such as fibers, dust, oil droplets or condensation circulating in enclosure 52 from being sampled. The filter assembly 28 should reside fully within enclosure 52, at the furthest inward extension of the probe 20.

The initial entry of the moist process atmosphere is through the filter assembly 28. The relative position of filter assembly 28 to the probe 20 may be changed by the straight length of the connecter pipe 30 to which it is threaded. Insulated enclosure walls 42, 12" thick or greater, might necessitate this change. Further, a more representative humidity sample may be obtained by extending the filter assembly 28 in applications where the desired measurement is a considerable distance from the enclosure wall 42. For example, exhaust flues of 5 feet square are not uncommon in commercial applications. The connector pipe 30 may be a flexible, circuitous lineal member to measure humidity at a point in the enclosure 52 which may be otherwise difficult to sample by a straight path connection.

Figure 8:
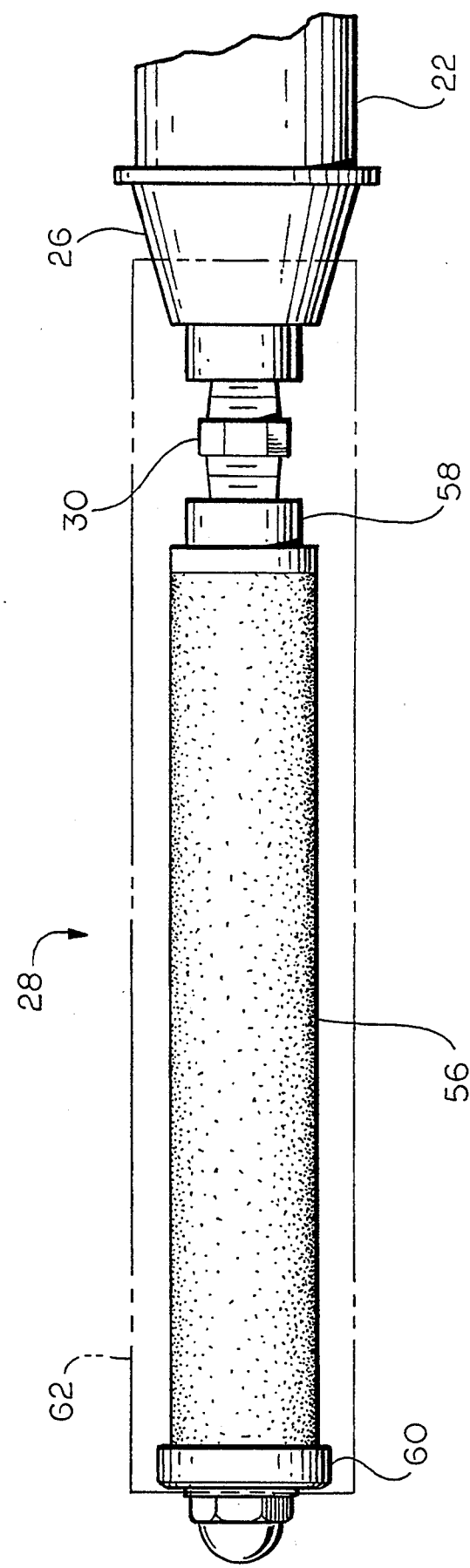
FIG. 8 is a sketch of the filter assembly showing the respective orientation of the components.

Referring to FIG. 8, the filter assembly 28 is designed for manual cleaning and disassembly without tools. The filter assembly 28 is comprised of a filter element 56, support stem 58, filter cap 60, and cover tube 62. All filter components are 300 series stainless steel. The cover tube 62 is rigid walled tubing open only at the probe 20 end. The cover tube 62 protects the filter element 56 from physical abuse. The support stem 58 is bored and partially threaded. Perimeter holes extend through the stem 58 wall. The filter element 56 is held in compression by threading the cap 60 to the stem 58. The cover tube 62 is supported from the threaded extension of the stem 50. The filter element 56 is a porous, sintered, cylindrical metal element of no greater than 15 micron filter rating. The filter element 56 is manufactured by Mott Metallurgical, Farmington, Conn.

Figure 9:
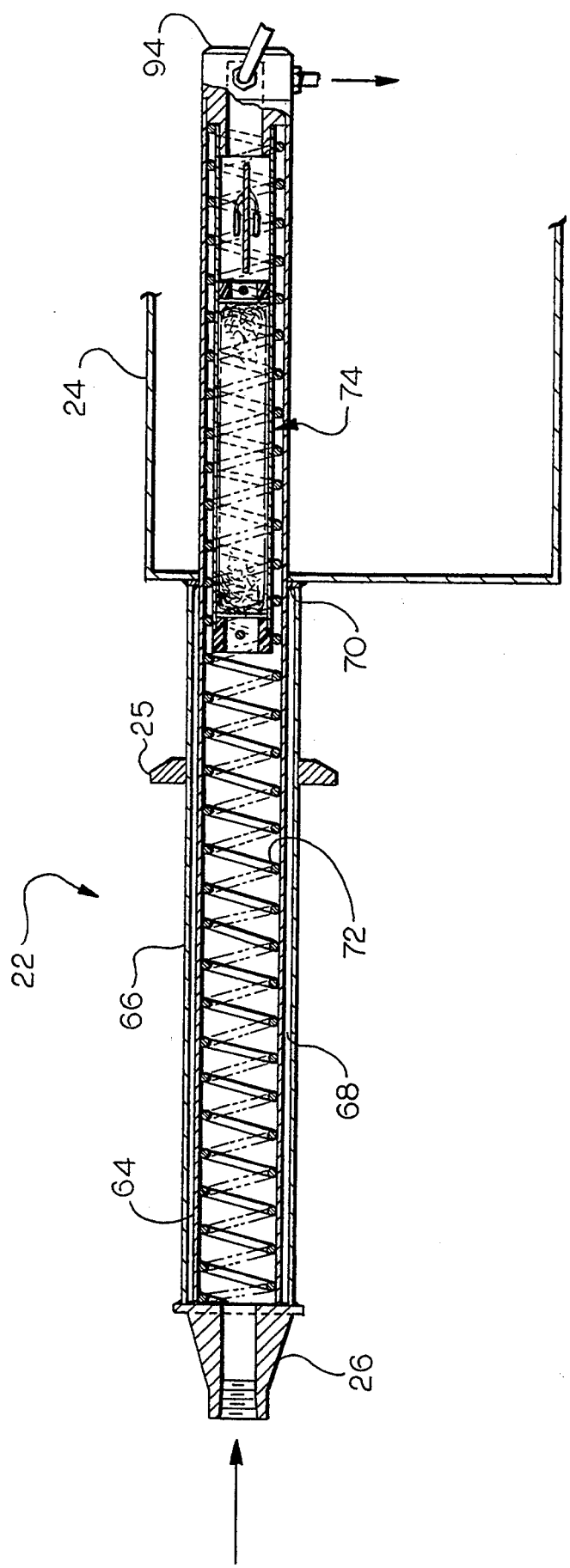
FIG. 9 is a sectional diagram of the instrument probe barrel showing the spatial relationship of the internal components and external tubular structure.

Referring to FIG. 9, the internal geometry of the probe barrel 22 is shown in section view. Two lengths of nominal 16 GA (0.065 wall) stainless steel tubing comprise the main structure of the barrel 22. The internal flow tube 64 is concentric within an external convection tube 66. The flow tube 64 is of a greater length than the convection tube 66 and extends within the probe back 24. The flow tube 64 and convection tube 66 are separated by a clearance gap 68, nominally 1/16" wide, the length of the convection tube 66. The gap 68 is sealed by continuous welding at port 26 and a concentric ring 70.

A sample from enclosure 52 passes through filter assembly 28, connector pipe 30 and port 26, and along the full interior length of the flow tube 64. An electrical heater 72 of helix construction is in intimate with the internal perimeter of flow tube 64. The heater is a constant diameter, constant pitch helix such that heat transfer will be applied equally and uniformly to the total perimeter and full lineal length of flow tube 64. The heater 72 is constructed of two high temperature resistance wires insulated with magnesium oxide inside a 1/16" diameter stainless steel sheath. The heater is rated to continuous service temperatures of approximately 1250° F. The heater 72 is termed a cable heater, and manufactured by Watlow Electric Mfg. Co., St. Louis, Mo.

Figure 10:
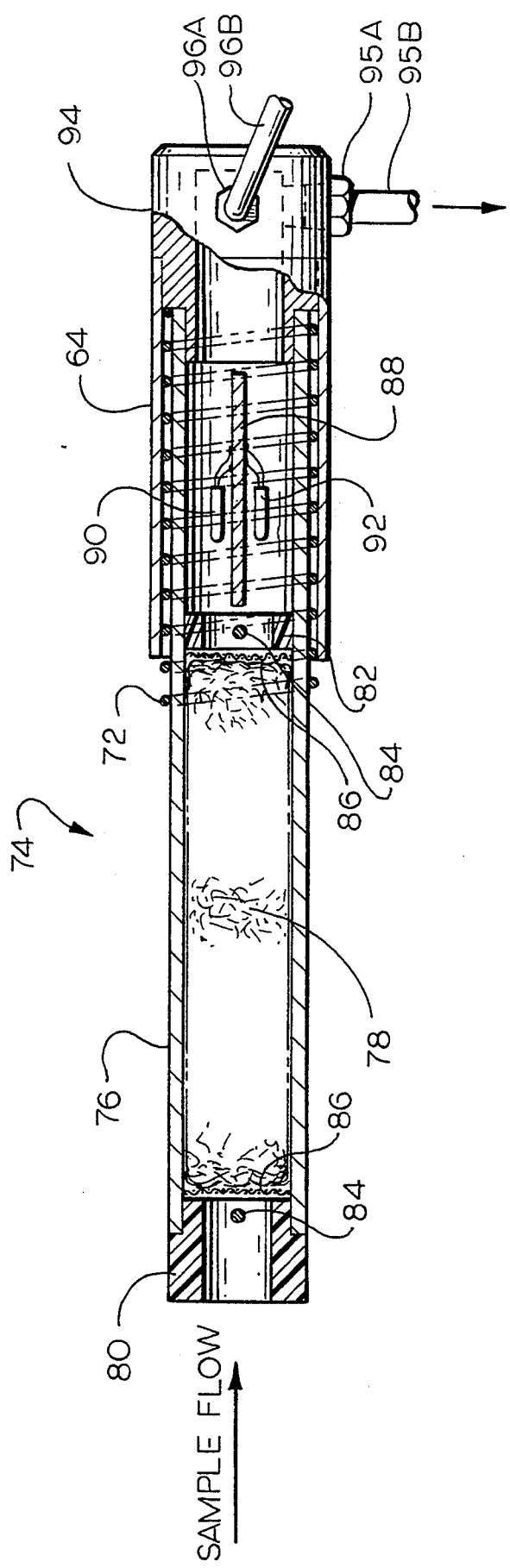
FIG. 10 is a sectional diagram of the diffuser assembly containing humidity and temperature sensors, a packing material, and construction features such that the flow sample is regulated to a constant measurement temperature.

Referring to FIG. 10, the diffuser assembly 74 incorporates a cylinder of high thermally conductive material. In this embodiment, the diffuser cylinder 76 is machined from copper pipe to fit closely within the internal helix diameter of heater 72. A packing material 78 is compressed tightly within the diffuser cylinder 76. The packing material 78 is a 300 series stainless steel textile mesh manufactured by Metex Corp of Edison, N.J. The packing 78 is constrained by drilled bushings 80, 82 of high temperature resistant material, preferably teflon. The bushings 80, 82 are staked in place through the cylinder 76 wall by pins 84. Mesh screens 86 ensure that the packing remains stationary.

A rectangular circuit board 88 fits on edge within the cylinder 76. A humidity measuring sensor 90 and temperature measuring sensor 92 are soldered to opposite sides of the circuit board 88 at the same cross-sectional plane of the diffuser assembly 74. The sensors are positioned in such a manner to be completely immersed in the flowing ambient atmosphere.

The temperature sensor 92 is a RTD (resistive temperature device) selected for high accuracy and temperature capability. Model F3142 of Omega Technologies Co., Stamford, Conn. is a representative device.

The humidity sensor 90 is a solid state relative humidity sensor which measures relative humidity as a function of moisture content and temperature of the surrounding ambient. A humidity sensor which operates at elevated temperatures above 220° F. and is unaffected by water condensate, products of combustions and most reagent vapors are preferred in this environment. The humidity sensor 90 is a thin film capacitive RH sensor. The RH sensor is the Model #H6100 manufactured by Coreci Corp of Lyon, France and distributed by Coreci Corp, Austin. Tex. The RH sensor has a broad measurement range of 5 to 95% RH, low hysteresis, and fast response times.

The diffuser cylinder 76 is bonded in a fluid-tight manner to backplug 94. A high temperature potting compound, such as flexible silicone, is used. A shielded electrical cable 96B passes through a constrictive fitting 96A for connection to the circuit board 88.

The sample exhausts through a hose barb 95A, to exhaust tubing 95B. Tubing 95B is integrated within a pneumatic circuit (not shown). The circuit includes a flow-inducing means such as the venturi pump 54, forcing a continuous sample from the enclosure 52 to traverse the length of the flow tube 64 and diffuser assembly 74 for humidity measurement. Condensate and spent atmosphere discharge to atmospheric pressure at drain 34.

9. Operation of Instrument

In operation, the instrument probe 20 provides a continuous measurement of process humidity from the enclosure 52. The probe 20 is mated to mounting tube 46 in an air-tight fashion. Supported by the clamp assembly 44, the probe barrel 22 extends through the mounting tube 46, with the filter assembly 28 at a location of desirable humidity measurement within the enclosure 52. The probe back 24 is within the room temperature ambient of the process plant 53. The enclosure 52 may be a conveyorized oven or exhaust stack or similar process environment, the absolute pressure of which is approximately at the prevailing external barometric pressure. A sample of moist process air is induced to flow in a controlled rate from the enclosure 52. The sample is drawn through the probe 20 by means of a slight negative pressure. Preferably the negative pressure is developed by an aspirating venturi pump 54 integrated within a pneumatic circuit, located in probe back 24. A slight positive pressure source may not require any additional flow inducing means by being at a higher pressure than that of the external ambient.

Moist air initially enters the open-end of protective cover tube 62 and flows through the sintered filter element 56. The moist air sample, filtered of particulates and product contaminants, enters perimeter holes in the support stem 58, and continues through the connector pipe 30 and the tapered port 26. Filter assembly 28, connector pipe 30, and port 26 extend within the enclosure 52 and have equilibrated in temperature to the process atmosphere. This prevents the sample from condensing while traversing through these elements which might otherwise require a heater.

The probe barrel 22 is a heat exchanger. The sample air is regulated in temperature by energy exchange with the walls of the flow tube 64. The internal wall of the flow tube 64 is in intimate contact with the heater 72. The temperature at any point in the flow tube 64 is held above the dew point temperature of enclosure 52 by the heater 72. The local temperature along the flow tube 64 length varies due to the heater 54 and the local temperature of convection tube 66. The temperature along the length of convection tube 66 varies in accordance with the convection tube 66 location. The local temperatures along the convection tube 66 length approach the immediate outside external temperature by natural convection. A temperature gradient from the process temperature to room temperature develops. In a high temperature process enclosure, the temperature along the convection tube 66 length reduces in value in the flow direction. Temperatures along the flow tube 64 follow the temperature changes in the convection tube 66, by convection and radiation across the gap 68. Since the flow tube 64 and connection tube 66 are fabricated from stainless steel, a very poor thermal conducting material, wall temperatures of tubes 64, 66 do not readily change by conduction along the length dimension of tubes 64 and 66. From a high temperature process, the result is a uniform reduction in temperature along the flow tube 64 length, in the flow direction. The moist air sample in contact with the flow tube 64 wall, correspondingly reduces in temperature approaching the measurement temperature. The gap 68 functions as a thermal insulator. The gap 68 limits the energy transfer between flow tube 64 and convection tube 68. Energy required from the heater 72 is reduced and handling surfaces of the barrel 22 are maintained at lower temperatures.

The flow rate of the sample is controlled between 1 and 5 CFH. High flow rates reduce the response time of the device by increasing the sampling rate, particularly in changing moisture conditions. Lower flow rates are preferred to extend the time intervals between filter maintenance. In all cases, the potential for low flow rates within the diameter of the flow tube 64 results in laminar flow velocities, approximately 2.5 inches/second maximum. The diffuser assembly 74 prevents the flowing sample from stratifying or otherwise containing temperature discontinuities. The diffuser cylinder 76 is a material of high thermal conductivity, copper for example. Thermal conduction along the diffuser cylinder 76 length and high thermal contact with the packing material 78 to the cylinder 76 center ensures a region of very constant temperature. The sample is thoroughly mixed and equilibrates to the temperature of the diffuser assembly 74 while flowing through packing material 78. Though highly compressed, little pressure drop occurs while flowing through the diffuser assembly 74. This is due to the low sampling flow rates, the pressure drop being directly proportional to flow rate for laminar conditions. The local pressure of the moist air remains equivalent to that of the pressure in the enclosure 52. The packing material 78 also filters any trace contaminants from the sample due to the high surface area in contact with the gas. Mesh screens 86 trap the packing material 78 and provide additional filtering.

After flowing through the packing material 78, the gas temperature is uniform and equal to the desired measurement temperature. Humidity measurements may be at any ambient temperature in excess of the ambient source humidity temperature and below the operational limit of the humidity and temperature sensors. In this embodiment, the moist air is regulated to 215° F., plus or minus 0.1° F. Measurement temperatures above the boiling point of water are preferred. Commercially available RH sensors are highly non-linear and tend to saturate in atmospheres above 95% RH. Operating the sensor above 212° F. reduces the non-linearibility in high humidity measurements. For example, the maximum % RH at 215° F., 1 ATM is 94.2%. At higher elevations the maximum % RH is lower. Maintaining the measurement temperature above the boiling point has a secondary advantage. Migration of the water vapor molecules into and out of the hydroscopic material core of thin film RH sensors and equivalent devices is greatly accelerated. Response times at elevated temperature are a fraction of the response time at room temperature. Further, any water that may condense on the sensor or in the sensor environment is quickly evaporated in operation. At lower operating temperatures, the presence of liquid water influences the true humidity measurement.

The flowing sample in thermal contact with the diffuser assembly 74 is regulated to the desired constant measurement temperature. The measurement temperature is controlled at the point of humidity measurement. The moist air at constant temperature flows over temperature measuring sensor 92, in the same cross sectional plane as the humidity measuring sensor 90. The temperature of the sample is measured by the temperature sensor 92. Proportional based circuitry is integrated with the temperature sensor 92 and heater 72 for closed loop constant measurement temperature control. The energy output of the heater 72 is then adjusted based on the deviation from the desired measurement temperature. The diffuser assembly 74 changes temperature and corrects the sample temperature toward setpoint.

Exposure of the humidity measuring sensor 90 to the flowing sample produces a measurable electrical change. In this embodiment, the change in humidity sensor 90 capacitance is linear to changes in relative humidity. The capacitance change is electronically compared to the capacitance change required for maximum relative humidity at the measurement temperature. The ratio is multiplied by 100 to obtain a percentage in normalized relative humidity. The humidity measuring sensor 90 continues to change in electrical output in response to changes in humidity of the flowing gas sample. The gas, once measured, is exhausted to atmosphere through drain 34. Instrument circuitry is available to output the RHN percentage for display on a digital indicator 17 and provide instrument control signals of 0–5 VDC or 4–20 mA.

The technology is commercially viable for industrial control applications. In control applications, the instrument probe 20 would output the control signal to a smart controller 18. The controller 18 would receive the signal and output a second signal, as programmed, to control secondary 19 equipment such as exhaust damper position, control valves, fan speed, or alarms. Any change in the moisture content of the enclosure 52 would be measured by the instrument probe 20, and then processed by the controller 18 which would change the operation of secondary equipment 19, effectively forming a closed control loop based on humidity in the source atmosphere.

The description of the preferred embodiments have been presented for purposes of illustration. The description is not intended to be exhaustive or to limit the invention to the precise form disclosed. Many modifications and variations are possible. It is therefore understood that the scope of the invention is not to be limited by this detailed description but rather by the appended claims.

What is claimed:

1. A process for humidity measurement comprising the steps of:
   regulating the temperature of a sample to a temperature above the dew point temperature of the humidity source,
   regulating the temperature of said sample to a temperature below the operational limit of a humidity measurement sensor,
   maintaining the sample temperature at a constant predetermined measurement temperature,
   measuring the relative humidity of said sample at said constant temperature, and
   calculating the absolute moisture content of said sample based solely on sensed relative humidity and absolute measurement pressure.

2. The process of claim 1 further comprising the step of determining said absolute measurement pressure by correlation with standard barometric pressure at the elevation above sea level at which the relative humidity is measured.

3. The process of claim 1 wherein said absolute moisture content is calculated in values of normalized relative humidity.

4. The process of claim 1 wherein said constant measurement temperature is above the saturation temperature at the measurement pressure.

* * * * *